United States Patent [19]

Ruggeri et al.

[11] Patent Number: 5,798,216
[45] Date of Patent: Aug. 25, 1998

[54] ANTIBODIES AND IMMUNOASSAYS FOR DETECTING PLATELET TRANSFUSION REFRACTORINESS

[75] Inventors: Zaverio M. Ruggeri, La Jolla; Jerry L. Ware, Encinitas, both of Calif.

[73] Assignee: The Scripps Research Institute, La Jolla, Calif.

[21] Appl. No.: 470,137

[22] Filed: Jun. 6, 1995

Related U.S. Application Data

[62] Division of Ser. No. 817,852, Jan. 6, 1992, Pat. No. 5,427,939.

[51] Int. Cl.⁶ .................. G01N 33/567; G01N 33/537
[52] U.S. Cl. .................. 435/7.21; 436/503; 436/538
[58] Field of Search .................. 530/387.1, 387.2, 530/387.9, 388.25; 435/7.21, 70.21, 172.2, 240.27; 436/503, 538

[56] References Cited

U.S. PATENT DOCUMENTS

| | | | |
|---|---|---|---|
| 4,810,632 | 3/1989 | McMillan et al. | 435/7 |
| 4,959,308 | 9/1990 | Ogden | 435/7 |

OTHER PUBLICATIONS

Platelet Immunobiology, Molecular and Clinical Aspects. Kunicki, J.T. and George, J.N., chapters 6 and 19, J.B. Lippincott, Philadelphia, 1989.
Shulman, N.R. et al., *Prog. Hematol.*, 4, 222, (1964).
Kuijpers, R. et al., *Blood*, 74, 226a, (1989) (abstract).
Yamamoto, K. et al. *Thromb. Res.*, 43, 41–55 (1986).
Ware, J. et al., *Blood*, 78(10), abstract 278a, Dec. 1991.
Ware, J. et al., *Thrombosis and Hemostasis*, 65(6), 770 (1991), abstract 347.
Murata, M. et al., *J. Biol. Chem.*, 266, 15474–15480 (1991).
Saji, H. et al., *Vox Sang.* 56, 283 (1989).
Ishida, F. et al., *Blood*, 78, 1722 (1991).
Lopez, J.A. and Ludwig, E.H., *Clin. Res.*, 39(2), 327a (1991)—"Molecular Basis of Platelet Glycoprotein Ib Polymorphism".
Titani, K. et al., *Proc. Natl. Acad. Sci. USA*, 84, 5610–5614 (1987).
Lopez et al., *Proc. Natl. Acad. Sci. USA*, 84, 5615–5617 (1987).
Wenger, R.H. et al. *Biochemical and Biophysical Research Comunications*, 156(1), 389–395 (1988).
Handa, M. et al., *J. Biol. Chem.*, 261, 12579–12585 (1986).
Vicente, V. et al., *J. Biol. Chem.*, 265(1), 274–280 (1990).
Kuijpers et al., *J. Clin. Invest.*, 89, pp. 381–384 (Feb. 1992).
Kickler et al., *Transfusion*, 30(7), pp. 622–625 (Sep. 1990).
Kunkel, T.A., *Methods. Enzymol.*, 154, 367–383 (1987).
Blin, N. et al., *Nucleic Acid Res.*, 3, 2303 (1976).
Kuijpers et al., *The Lancet*, vol. 336, No. 8726, p. 1319 (Nov. 24, 1990).
von Heijne, G., *J. Mol. Biol.*, 184, 99–105 (1985).
Houghten, R.A., *Proc. Natl. Acad. Sci. USA*, 82, 5131–5135 (1985).
Petersen et al., *Clinical Research*, 37(2), 549A (1989).
Wicki et al., *Thrombosis and Haemostasis*, 61(3), 448–453 (1989).
Johnstone et al. (Immunochemistry in Practice, 2nd edition, Blackwell Scientific Publications, Osney Mead, Oxford OX2 OEL pp. 30–47 1987.
Harlow et al. Antibodies a laboratory Manual, Cold Spring Harbor, Cold Spring Harbor, New York 11724, pp. 27, 28, 141, 1988.
Marcelli–Barge et al. (1973) Vox Sang. vol. 24 (1–11).
Kuijpers et al. (Jan. 1, 1992) Blood, vol. 79(1):283–288.
Von dem Borne et al. (1980) Vox. Sang. vol. 39 113–120.
Murata et al. (Jun. 1, 1992) Blood vol. 79(11):3086–3090.
Wautier et al. (1993) Nouv. Rev. Fr. Hematol. vol. 35:171–178.

*Primary Examiner*—Frank C. Eisenschenk
*Assistant Examiner*—Patrick Nolan
*Attorney, Agent, or Firm*—Synnestvedt & Lechner

[57] ABSTRACT

A method of inhibiting platelet transfusion refractoriness comprising administering third-party platelets to a patient whose platelet glycoprotein Ibα polypeptides expressed from the patient's DNA have been determined to have either threonine or methionine residues, or both, at amino acid residue position 145 thereof, the third-party platelets having expressed at residue position 145 of the glycoprotein Ibα polypeptide thereof amino acids that are the same as those expressed on the glycoprotein Ibα polypeptides of the patient's platelets. Also, an antibody, or a fragment thereof, in substantially pure form having as its target epitope a domain of glycoprotein Ibα, the affinity of the antibody, or fragment thereof, for said epitope being dependent on the identity of the amino acid residue at position 145 of the glycoprotein. In addition, in a process for storing a supply of platelets for therapeutic use in a patient, the improvement comprising segregating the platelets into three stocks dependent upon whether residue 145 of glycoprotein Ibα polypeptides of the platelets includes: (A) threonine; (B) methionine; or (C) both threonine and methionine. Also, a method of immunoassay comprising contacting a sample of blood, or a composition derived therefrom, with alloantigenic Thr or Met$^{145}$ form of glycoprotein Ibα, or a fragment thereof, containing the Thr/Met$^{145}$ locus, and determining whether there is present a complex of antibody and a form of the glycoprotein or a fragment thereof.

4 Claims, 2 Drawing Sheets

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
    ( A ) LENGTH: 906
    ( B ) TYPE: Nucleic Acid
    ( C ) STRANDEDNESS: Single stranded
    ( D ) TOPOLOGY: Linear ( x i ) SEQUENCE DESCRIPTION: SEQ ID NO: 1:

| CAC | CCC | ATC | TGT | GAG | GTC | TCC | AAA | GTG | GCC | 30 |
|---|---|---|---|---|---|---|---|---|---|---|
| His | Pro | Ile | Cys | Glu | Val | Ser | Lys | Val | Ala | |
| | | | | 5 | | | | | 10 | |
| AGC | CAC | CTA | GAA | GTG | AAC | TGT | GAC | AAG | AGG | 60 |
| Ser | His | Leu | Glu | Val | Asn | Cys | Asp | Lys | Arg | |
| | | | | 15 | | | | | 20 | |
| AAT | CTG | ACA | GCG | CTG | CCT | CCA | GAC | CTG | CCG | 90 |
| Asn | Leu | Thr | Ala | Leu | Pro | Pro | Asp | Leu | Pro | |
| | | | | 25 | | | | | 30 | |
| AAA | GAC | ACA | ACC | ATC | CTC | CAC | CTG | AGT | GAG | 120 |
| Lys | Asp | Thr | Thr | Ile | Leu | His | Leu | Ser | Glu | |
| | | | | 35 | | | | | 40 | |
| AAC | CTC | CTG | TAC | ACC | TTC | TCC | CTG | GCA | ACC | 150 |
| Asn | Leu | Leu | Tyr | Thr | Phe | Ser | Leu | Ala | Thr | |
| | | | | 45 | | | | | 50 | |
| CTG | ATG | CCT | TAC | ACT | CGC | CTC | ACT | CAG | CTG | 180 |
| Leu | Met | Pro | Tyr | Thr | Arg | Leu | Thr | Gln | Leu | |
| | | | | 55 | | | | | 60 | |
| AAC | CTA | GAT | AGG | TGC | GAG | CTC | ACC | AAG | CTC | 210 |
| Asn | Leu | Asp | Arg | Cys | Glu | Leu | Thr | Lys | Leu | |
| | | | | 65 | | | | | 70 | |
| CAG | GTC | GAT | GGG | ACG | CTG | CCA | GTG | CTG | GGG | 240 |
| Gln | Val | Asp | Gly | Thr | Leu | Pro | Val | Leu | Gly | |
| | | | | 75 | | | | | 80 | |
| ACC | CTG | GAT | CTA | TCC | CAC | AAT | CAG | CTG | CAA | 270 |
| Thr | Leu | Asp | Leu | Ser | His | Asn | Gln | Leu | Gln | |
| | | | | 85 | | | | | 90 | |
| AGC | CTG | CCC | TTG | CTA | GGG | CAG | ACA | CTG | CCT | 300 |
| Ser | Leu | Pro | Leu | Leu | Gly | Gln | Thr | Leu | Pro | |
| | | | | 95 | | | | | 100 | |
| GCT | CTC | ACC | GTC | CTG | GAC | GTC | TCC | TTC | AAC | 330 |
| Ala | Leu | Thr | Val | Leu | Asp | Val | Ser | Phe | Asn | |
| | | | | 105 | | | | | 110 | |
| CGG | CTG | ACC | TCG | CTG | CCT | CTT | GGT | GCC | CTG | 360 |
| Arg | Leu | Thr | Ser | Leu | Pro | Leu | Gly | Ala | Leu | |
| | | | | 115 | | | | | 120 | |
| CGT | GGT | CTT | GGC | GAA | CTC | CAA | GAG | CTC | TAC | 390 |
| Arg | Gly | Leu | Gly | Glu | Leu | Gln | Glu | Leu | Tyr | |
| | | | | 125 | | | | | 130 | |
| CTG | AAA | GGC | AAT | GAG | CTG | AAG | ACC | CTG | CCC | 420 |
| Leu | Lys | Gly | Asn | Glu | Leu | Lys | Thr | Leu | Pro | |
| | | | | 135 | | | | | 140 | |
| CCA | GGG | CTC | CTG | ATG | CCC | ACA | CCC | AAG | CTG | 450 |
| Pro | Gly | Leu | Leu | Met | Pro | Thr | Pro | Lys | Leu | |
| | | | | 145 | | | | | 150 | |
| GAG | AAG | CTC | AGT | CTG | GCT | AAC | AAC | AAC | TTG | 480 |
| Glu | Lys | Leu | Ser | Leu | Ala | Asn | Asn | Asn | Leu | |

|     |     |     |     | 155 |     |     |     | 160 |     |
|-----|-----|-----|-----|-----|-----|-----|-----|-----|-----|
| ACT | GAG | CTC | CCC | GCT | GGG | CTC | CTG | AAT | GGG | 510
| Thr | Glu | Leu | Pro | Ala | Gly | Leu | Leu | Asn | Gly |
|     |     |     |     | 165 |     |     |     | 170 |     |
| CTG | GAG | AAT | CTC | GAC | ACC | CTT | CTC | CTC | CAA | 540
| Leu | Glu | Asn | Leu | Asp | Thr | Leu | Leu | Leu | Gln |
|     |     |     |     | 175 |     |     |     | 180 |     |
| GAG | AAC | TCG | CTG | TAT | ACA | ATA | CCA | AAG | GGC | 570
| Glu | Asn | Ser | Leu | Tyr | Thr | Ile | Pro | Lys | Gly |
|     |     |     |     | 185 |     |     |     | 190 |     |
| TTT | TTT | GGG | TCC | CAC | CTC | CTG | CCT | TTT | GCT | 600
| Phe | Phe | Gly | Ser | His | Leu | Leu | Pro | Phe | Ala |
|     |     |     |     | 195 |     |     |     | 200 |     |
| TTT | CTC | CAC | GGG | AAC | CCC | TGG | TTA | TGC | AAC | 630
| Phe | Leu | His | Gly | Asn | Pro | Trp | Leu | Cys | Asn |
|     |     |     |     | 205 |     |     |     | 210 |     |
| TGT | GAG | ATC | CTC | TAT | TTT | CGT | CGC | TGG | CTG | 660
| Cys | Glu | Ile | Leu | Tyr | Phe | Arg | Arg | Trp | Leu |
|     |     |     |     | 215 |     |     |     | 220 |     |
| CAG | GAC | AAT | GCT | GAA | AAT | GTC | TAC | GTA | TGG | 690
| Gln | Asp | Asn | Ala | Glu | Asn | Val | Tyr | Val | Trp |
|     |     |     |     | 225 |     |     |     | 230 |     |
| AAG | CAA | GGT | GTG | GAC | GTC | AAG | GCC | ATG | ACC | 720
| Lys | Gln | Gly | Val | Asp | Val | Lys | Ala | Met | Thr |
|     |     |     |     | 235 |     |     |     | 240 |     |
| TCT | AAC | GTG | GCC | AGT | GTG | CAG | TGT | GAC | AAT | 750
| Ser | Asn | Val | Ala | Ser | Val | Gln | Cys | Asp | Asn |
|     |     |     |     | 245 |     |     |     | 250 |     |
| TCA | GAC | AAG | TTT | CCC | GTC | TAC | AAA | TAC | CCA | 780
| Ser | Asp | Lys | Phe | Pro | Val | Tyr | Lys | Tyr | Pro |
|     |     |     |     | 255 |     |     |     | 260 |     |
| GGA | AAG | GGG | TGC | CCC | ACC | CTT | GGT | GAT | GAA | 810
| Gly | Lys | Gly | Cys | Pro | Thr | Leu | Gly | Asp | Glu |
|     |     |     |     | 265 |     |     |     | 270 |     |
| GGT | GAC | ACA | GAC | CTA | TAT | GAT | TAC | TAC | CCA | 840
| Gly | Asp | Thr | Asp | Leu | Tyr | Asp | Tyr | Tyr | Pro |
|     |     |     |     | 275 |     |     |     | 280 |     |
| GAA | GAG | GAC | ACT | GAG | GGC | GAT | AAG | GTG | CGT | 870
| Glu | Glu | Asp | Thr | Glu | Gly | Asp | Lys | Val | Arg |
|     |     |     |     | 285 |     |     |     | 290 |     |
| GCC | ACA | AGG | ACT | GTG | GTC | AAG | TTC | CCC | ACC | 900
| Ala | Thr | Arg | Thr | Val | Val | Lys | Phe | Pro | Thr |
|     |     |     |     | 295 |     |     |     | 300 |     |
| AAA | GCC |     |     |     |     |     |     |     |     | 906
| Lys | Ala |     |     |     |     |     |     |     |     |
|     | 302 |     |     |     |     |     |     |     |     |

ANTIBODIES AND IMMUNOASSAYS FOR DETECTING PLATELET TRANSFUSION REFRACTORINESS

This is a divisional of application Ser. No. 07/817,852 filed on Jan. 6, 1992, now U.S. Pat. No. 5,427,939.

This invention was made with government support under HL 42846 awarded by the National Institutes of Health. The government has certain rights in the invention.

FIELD OF THE INVENTION

This invention relates to providing patients with blood products that minimize recognition and response thereto by the recipient's immune system.

The fundamental function of the immune system of the body includes detecting foreign macromolecules that have invaded the body (such as those produced by or attached to a microorganism), distinguishing them from molecules produced by the body (self-molecules), and then producing specific cells and molecules (antibodies) that combine with the foreign macromolecules to inactivate them and eventually destroy them.

The immune system functions in part by maintaining a library of cells, each of which is capable of producing a specific antibody that binds to a specific foreign macromolecule, the macromolecule being free in solution or attached to a foreign cell. An antibody is a protein that binds specifically to a foreign macromolecule at an epitope therein, leading to inactivation of the macromolecule that contains the epitope. An epitope is a structural domain or subregion of the macromolecule having a unique structure (for example, charge distribution and shape) that is recognized and targeted by the immune system. Normally, epitopes on self-molecules go unrecognized, that is, the immune system does not identify them as representing foreign structures against which a defense must be made.

In order to function effectively, the immune system must be sensitive, that is, it must be able to detect those differences in structure (which are often very subtle) between "self molecules" and foreign molecules. These differences may include amino acid substitutions in proteins and/or differences in the type or orientation of carbohydrate and lipid components attached to macromolecules, including proteins, glycoproteins, glycolipids and lipoproteins.

There are times when it is clinically desirable to give to a patient who has suffered blood loss associated with surgery or injury, foreign blood products, including cells, such as, for example, a transfusion of blood products collected from one or more donors. One type of therapeutic blood product comprises platelets. Platelets are non-nucleated, discoid, cell-like structures which are 2–5 microns in diameter and which are derived from megakaryocytic blood cells. They are crucial to the formation of clots, such as are necessary to heal an injury to a blood vessel, and are often administered to patients to facilitate clot formation.

Platelets are believed to participate in clot formation as follows. The restriction or termination of the flow of blood within the circulatory system in response to a wound involves a complex series of reactions which can be divided into two processes, primary and secondary hemostasis.

Primary hemostasis refers to the process of platelet plug or soft clot formation. Effective primary hemostasis is accomplished by platelet adhesion, that is, the interaction of a platelet with the surface of damaged vascular endothelium on which are exposed underlying collagen fibers and/or other adhesive macromolecules such as proteoglycans and glycosaminoglycans to which platelets bind; and platelet activation.

Secondary hemostasis involves the reinforcement or cross-linking of the soft platelet clot. This secondary process is initiated by proteins circulating in the plasma (coagulation factors) which are activated during primary hemostasis in response to a wound. The activation of these factors results ultimately in the production of a polymeric matrix of the protein fibrinogen (then called "fibrin") which reinforces the soft clot.

There are, however, potential problems associated with administering third party blood products to a patient in need thereof. It has been recognized that there is a natural genetic variation within the DNA of individuals that encodes the protein components of blood products, including those of platelets, or that encodes the proteins that catalyze the assembly of such macromolecular components thereby determining their structure. The immune system of an individual may respond to the resultant differences, such as amino acid substitutions in proteins, interpreting them to define foreign epitopes. Organ transplant rejection is a well known result of such a response. Accordingly, blood products are routinely typed, that is, screened for particular epitopes within the macromolecules thereof to minimize the potential adverse response of a recipient's immune system to blood products of a donor.

The most widely recognized groups of epitopes against which blood products are typed are: (A) the ABO system that arises from differences in carbohydrate attached to large lipid molecules inserted into the plasma membrane of red blood cells and also of platelets; and (B) the Rh antigens. Although a number of relatively rare epitopes exist, the large majority of adverse immune responses to donor red blood cells are explained by a few well known epitopes. This invention pertains to identification of an important epitope of platelets.

An additional group of molecules, the HLA glycoproteins, found on the surface of red blood cells and platelets are also recognized by the immune system of transfusion recipients. Immune system response to HLA glycoprotein decreases strongly the likelihood of survival of transplanted organs or of transfused blood products, including platelets. Although proper typing of platelets with respect to HLA glycoprotein has reduced the incidence of platelet transfusion refractoriness, there exist certain additional surface components of platelets wherein variation in the structure thereof between donors and recipient strongly affects the likelihood of a successful program of platelet transfusion.

This invention identifies one such structural difference in a platelet surface component and pertains also to the administration of platelet-containing blood products, use of which minimizes adverse immune response in the recipients thereof. There follows hereafter a brief discussion of those factors that determine whether a genetically inherited structural difference in a platelet surface component will trigger an immune response by a transfusion recipient.

Generally the differences, such as amino acid substitutions, that define the particular forms of a protein present in different species are much greater than those differences that define the forms of the protein in different individuals of the same species. In general, the immune system is more likely to detect and respond to the differences (reflected in modified epitopes) that exist between species. Genetic variation between individuals of the same species is reflected in "alleles", that is, alternate forms of the gene that encodes a protein. Variation in the amino acid sequence of the protein results from minor differences (mutations) in the coding sequence of the gene. The different forms of the protein encoded by the alternate forms of the gene are termed alloantigens.

If the amino acid variants are such that they do not significantly alter the charge or shape of the domain (epitope) of the protein in which they are located, or trigger a conformational change elsewhere in the molecule, then the immune system may not recognize the difference between the products (alloantigens) of the two alleles. However, the forms of the protein may be sufficiently different so that antibodies (for example, in a transfusion recipient) can "determine" that one alloantigen is "self" and the other is foreign. Antibodies thus responding to the form of an epitope on one alloantigen, but not to the form of the epitope present on another alloantigen are termed "allotypes". Allotypic antibodies are particularly important in the practice of the invention because it is believed that identification of only a few important alloantigens on platelets is necessary to provide, in general, effective platelet transfusion.

REPORTED DEVELOPMENTS

A detailed discussion of platelet associated alloantigens is provided in Platelet Immunobiology, Molecular and Clinical Aspects, Kunicki, J. T. and George, J. N., chapters 6 and 19, J. B. Lippincott, Philadelphia, 1989. Representative alloantigen systems described therein include $P1^A$ and "Pen", both assigned to loci (amino acid sequence positions) on platelet glycoprotein IIIa, and "Bak" assigned to glycoprotein IIb. The $P1^E$ alloantigen system reported by Shulman, N. R. et al., Prog. Hematol., 4, 222, (1964) was later determined to be associated with an unidentified locus in glycoprotein Ibα. However, the locus was not identified, and the proband is now deceased.

An additional alloantigen system $Ko^a/Ko^b$ has been assigned to glycoprotein Ib-IX complex of platelets, Kuijpers, R. et al., Blood, 74, 226a, (1989) (abstract), but its locus has not been determined.

This invention defines the locus of a newly discovered platelet alloantigen system, provides for diagnostic screening procedures to detect both forms of the protein, and provides for administration to patients of typed platelets having improved functional characteristics.

SUMMARY OF THE INVENTION

Broadly stated, this invention is associated with the identification of an important locus (amino acid sequence position) on a protein of the platelet surface that is responsible for platelet transfusion refractoriness. The locus is located at residue 145 of platelet glycoprotein Ibα and is in the form of a threonine/methionine (abbreviated as "Thr/Met") amino acid dimorphism. Accordingly, there is provided a method of inhibiting platelet transfusion refractoriness comprising administering third-party platelets to a patient whose platelet glycoprotein Ibα polypeptides expressed from the patient's DNA have been determined to have either threonine or methionine residues, or both, at amino acid residue positions 145 thereof, said third-party platelets having expressed at residue position 145 of the glycoprotein Ibα polypeptide thereof amino acids that are the same as those expressed on the glycoprotein Ibα polypeptides of the patient's platelets.

The invention includes within its scope various strategies whereby potential platelet incompatibility between donor and recipient can be detected and avoided. An important strategy involves the use of an antibody, or a fragment thereof, in substantially pure form having as its epitope a domain of glycoprotein Ibα, the affinity of said antibody, or fragment thereof, for said epitope being dependent on the identity of the amino acid residue at position 145 of said glycoprotein.

An antibody of the invention in substantially pure form, whether monoclonal or polyclonal, is free of contamination by antibodies that have as epitope, domains of non-GPIbα polypeptide.

It is preferred in the practice of the invention that blood suppliers, for example, hospitals and blood banks, segregate their blood supplies based upon the dimorphism at the $Thr/Met^{145}$ locus. For this purpose, the invention provides a supply of blood product comprising platelets segregated into three stocks, one stock containing platelets having at position 145 on glycoprotein Ibα polypeptide thereof a threonine residue, a second stock containing platelets having at position 145 on glycoprotein Ibα polypeptides thereof a methionine residue, and a third stock containing platelets having at position 145 on the glycoprotein Ibα polypeptides thereof, methionine and threonine residues.

Another aspect of the present invention encompasses a process for providing a monoclonal antibody directed against a domain of glycoprotein Ibα, the epitope of said antibody being dependent on the presence of $Met^{145}$ or $Thr^{145}$ in said glycoprotein, said process comprising: (A) fusing a mixture of lymphocyte cells and myeloma cells to form hybridomas; the source of said lymphocyte cells being lymphocyte cells recovered from an animal that was immunized with glycoprotein Ibα, or a fragment thereof; (B) isolating a hybridoma that secretes an antibody directed against said epitope; (C) culturing said hybridoma; and (D) collecting the monoclonal antibody produced therefrom.

An additional aspect of the invention provides a method of immunoassaying utilizing an antibody, or a fragment thereof, to assay for human glycoprotein Ibα polypeptides for the presence therein of a $Met^{145}$ residue or a $Thr^{145}$ residue comprising contacting said antibody with glycoprotein Ibα polypeptides, or a fragment thereof, and determining whether said glycoprotein Ibα polypeptides, or fragment thereof, includes a $Met^{145}$ residue and/or a $Thr^{145}$ residue.

Another aspect of the invention provides for the determination of whether there has been administered previously to a patient a platelet-containing blood product containing at position 145 of the glycoprotein Ibα polypeptide thereof an amino acid residue different from the amino acid residue at position 145 of the patients glycoprotein Ibα polypeptide. Accordingly, there is provided a method of immunoassaying comprising contacting a sample of blood, or a composition derived therefrom, with alloantigenic Thr or $Met^{145}$ form of glycoprotein Ibα, or a fragment thereof containing said $Thr/Met^{145}$ locus, and determining whether there is present a complex of antibody and a form of said glycoprotein or a fragment thereof.

The invention includes also within its scope the provision of DNA sequences, expression plasmids, and recombinant host cells through which may be expressed glycoprotein Ibα polypeptide, or a fragment thereof, containing $Met^{145}$ or $Thr^{145}$ residues.

In one population of donors from Southern California, the $Thr^{145}$ allele was determined to be present about 89% of the time, whereas the $Met^{145}$ form was present at about 11%, leading to a population in which approximately 80% of individuals are homozygous for $Thr^{145}$, 2% are homozygous for $Met^{145}$ and 18% are heterozygous. The potential for platelet transfusion refractoriness is thus indicated.

BRIEF DESCRIPTION OF THE DRAWING

In FIG. 1 GPIbα is represented schematically. The GPIbα precursor protein consists of signal peptide (SP) and a 610-amino acid mature α-subunit. The mature α-subunit contains a series of leucine-rich repeats (LRR) within an N-terminal domain in which the binding site for von Willebrand factor is located; it also contains a transmembrane domain (TM) and a cytoplasmic tail.

FIG. 2 is a photograph of an agarose gel illustrating the AhaII restriction pattern obtained before (L) and after (R) restriction of human genomic DNA, encoding GPIbα, containing Thr$^{145}$ and/or Met$^{145}$ codons.

DETAILED DESCRIPTION OF THE INVENTION

Figure 1:
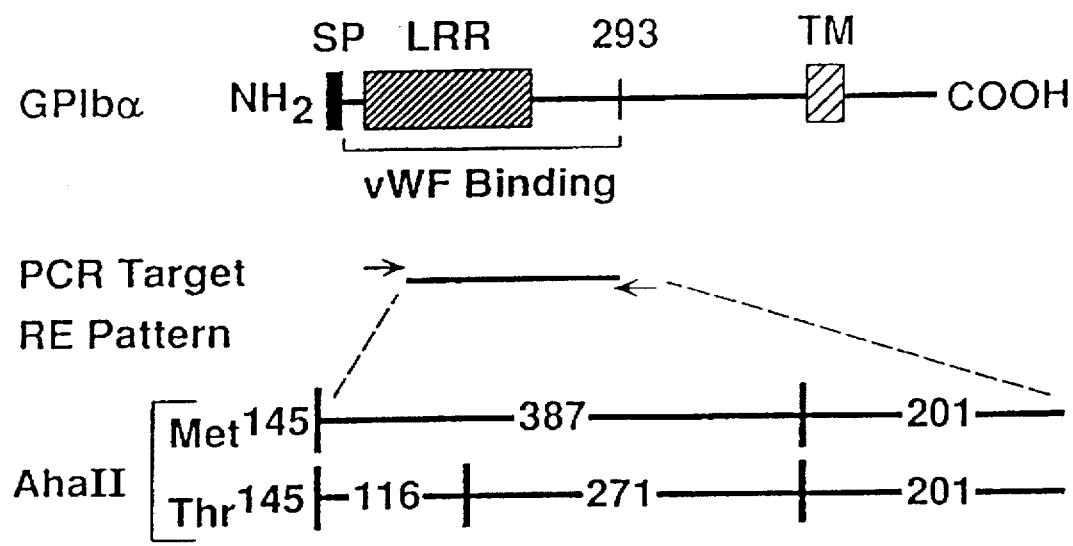
FIGS. 1 and 2 show the AhaII restriction pattern of human genomic DNA, encoding GPIbα, containing $Thr^{145}$ and/or $Met^{145}$ codons.

The terms "peptide" and "polypeptide" are used herein interchangeably. It is understood also that the practice of the invention pertains to the use of human blood products and proteins in human patients. The present invention encompasses also the use of glycoprotein Ibα polypeptides, or fragments thereof, (and/or the encoding DNA sequences therefor) that may contain, relative to the polypeptides and DNA sequences described herein that reflect the Thr/Met$^{145}$ polymorphism, additional mutations which do not affect the biological properties or diagnostic utility of the Thr$^{145}$- or Met$^{145}$-containing alloantigenic epitope of the polypeptides.

It is also within the scope of the invention to prepare modified forms of the glycoprotein Ibα polypeptides of the invention, such as by further or different mutation of an encoding DNA therefor, or by derivatization thereof (for example, sulfation, glycosylation, esterification, etc.). With respect to GPIbα polypeptides containing further or additional mutations, said GPIbα polypeptides (such as on donor platelets) are deemed equivalent in the practice of the invention if they have the functional properties of the alloantigen of a recipient and are not recognized by a recipient's immune system as being foreign. It should be understood also that the invention encompasses biologically unimportant differences between the actual DNA's and polypeptides utilized in the practice of the invention and the structural sequences of amino acids or nucleotides thereof as reported herein.

Introduction

In connection with the development of this invention, it has been found that the threonine/methionine dimorphism at residue 145 of the glycoprotein Ibα polypeptide of platelets defines an important alloantigen system that is a cause of platelet transfusion refractoriness, that is, an allosensitization to antigens found on platelets, such that additional platelet transfusion does not result in an increased platelet count.

For background purposes there is set forth hereafter information concerning glycoprotein Ibα polypeptide of platelets, and its role in clotting (hemostasis). The adhesion of platelets to damaged or diseased vessels occurs through mechanisms that involve specific platelet membrane receptors which interact with specialized adhesive molecules. One such platelet receptor is the glycoprotein Ib-IX complex which consists of a noncovalent association of two integral membrane proteins, glycoprotein Ib (GPIb) and glycoprotein IX (GPIX). GPIb, which is a two-chain molecule having an apparent molecular mass of approximately 160 kDa, is composed of a heavy (alpha, or "GPIbα") chain, having a molecular mass of approximately 145 kDa, linked by disulfide bonds to a light (beta, or GPIbβ) chain, having a molecular mass of approximately 22 kDa. GPIb is an integral membrane protein and both the alpha- and beta-chains described above have transmembrane domains. The term "glycocalicin" refers to a soluble proteolytic fragment of the heavy (α) chain of GPIb that is generated by cleavage in a position close to the transmembrane domain of the molecule (Yamamoto, K. et al. *Thromb. Res.*, 43, 41–55 (1986)). It is now clear that glycoalicin comprises most of the extracellular domains of the GPIbα from which it derives.

The adhesive ligand of the GPIb-IX complex is the protein von Willebrand factor ("vWF") which is found as a component of the subendothelial matrix, as a component of the α-granules secreted by activated platelets, and also as a circulating blood plasma protein. The actual binding site of vWF on the GPIb-IX receptor has been localized on the amino terminal (His$^1$-Arg$^{293}$) region of the α chain of glycoprotein Ib. This residue 1–293 region of the polypeptide may be generated as a fragment of GPIbα having a molecular weight of 45 kDa using, for example, trypsin to effect the necessary proteolytic cleavage. Inhibition of vWF-GPIbα interaction results in the prevention of primary hemostasis and the induction of an anti-thrombotic state useful in prevention of other diseases in which occlusion of blood vessels plays an important role. The interaction of GPIbα with vWF is believed to be unaffected by the Thr/Met$^{145}$ dimorphism of GPIbα polypeptide that is responsible for the immune phenomena detected in the practice of this invention. The amino acid sequence of the amino terminal 45 kDa fragment of GPIbα (residues His$^1$-Arg$^{293}$) has been reported by Titani, K. et al., *Proc. Natl. Acad. Sci. USA*, 84, 5610–5614 (1987).

A complete cDNA encoding human GPIbα polypeptide has been determined by Lopez et al., *Proc. Natl. Acad. Sci. USA*, 84, 5615–5617 (1987). The gene for GPIbα has been cloned from a genomic cosmid library utilizing a partial cDNA clone as a probe, and its sequence, including introns, has been determined by Wenger, R. H. et al. *Biochemical and Biophysical Research Communications*, 156(1), 389–395 (1988). The GPIbα sequence predicted thereby consists of a 16 amino acid signal peptide, Met$^{-16}$ through Pro$^{-1}$, followed by a 610 amino acid mature peptide or polypeptide region, His$^1$ through Leu$^{610}$. (The nucleotide numbering system of Wenger is used herein.) The structure and properties of GPIbα are reviewed in Ruggeri, Z. M., The Platelet Glycoprotein Ib-IX Complex, in *Progress in Hemostasis and Thrombosis*, vol. 10, p.3568, Coller, B. S. ed., W. B. Saunders Co., Philadelphia, 1991.

Discovery of the Thr$^{145}$/Met$^{145}$ Dimorphism of GPIbα

In connection with work to understand the molecular defect of platelet glycoprotein Ibα associated with the platelet disease "Bernard-Soulier Syndrome Type Bolzano" (an Ala$^{156}$→Val mutation), it was discovered that the genomic DNA of a propositus of the defect contained also a Thr$^{145}$→Met$^{145}$ codon substitution. The substitution was confirmed to be a naturally occurring amino acid dimorphism that does not affect the function of GPIbα with respect to its interaction with von Willebrand factor. Ware, J. et al., *Blood*, 78(10), abstract 278a, December 1991 abstract entitled "Ala$^{156}$→Val Substitution in Platelet Glycoprotein Ibα Impairs von Willebrand Factor Binding and is the Molecular Basis of Bernard-Soulier Syndrome Type Bolzano"; Ware, J. et al., *Thrombosis and Hemostasis*, 65(6), 770 (1991), abstract 347.

Practice of the Invention

This invention provides improved techniques of transfusion to a recipient of third-party blood products that contain platelets. The incidence and severity of platelet transfusion refractoriness is minimized following the practice of the invention. Representatives of the many aspects of the invention are three important techniques: (A) a method to determine (to type) the alloantigenic forms of glycoprotein Ibα of a patient so that the patient receives a transfusion of donor (third-party) platelets containing the identical alloantigenic form of GPIbα, for the Thr/Met$^{145}$ locus thereof; (B) a method of determining whether a patient who would otherwise benefit from third-party platelets (as, for example, in a transfusion) has produced antibody to previously administered platelets with respect to the Thr/Met$^{145}$ locus of glycoprotein Ibα; and (C) a method of determining in a donor the identity of alloantigenic forms of GPIbα, for the Thr/Met$^{145}$ locus thereof.

The following facts are of consideration in the administration to patients of blood products containing platelets. The practice of the invention increases the flexibility of the treatments patients may receive in connection therewith. As previously mentioned, third-party platelets, targeted by a recipient's immune system as containing foreign epitopes, become ineffective as clotting agents. It is known, however, that in a patient who has previously received no third-party platelets, for example, never having had a major accident or a surgical procedure, the immune response is sufficiently slow, on the order of weeks, that the patient would tolerate administration of said third-party platelets on which are expressed foreign epitopes for a period of time, such as needed to control bleeding after a surgical procedure. This flexibility is particularly important for administration of emergency medical treatment when supplies of properly typed and segregated platelets may not be available. With respect to patients to whom have been previously administered platelets and in whom an immune response was made, the diagnostic procedures of the invention provide warning of restrictions upon the alloantigenic forms (Thr/Met$^{145}$) which can be safely administered. Typing of third-party (donor) platelets to meet the above goals is similarly accomplished according to the invention.

Additionally, proper typing of platelets is particularly important with respect to treatment of cancer patients, particularly those having a leukemia and subject to chemotherapy and/or bone marrow irradiation and having low levels of platelet production. Such patients require frequent administration of platelets and are at risk of platelet transfusion refractoriness.

Preparation of Purified Antigen

In order to make the diagnostic antibody products of the invention, it is necessary that purified antigenic polypeptides be provided against which diagnostic antibodies can be prepared. Example 1 of the invention describes the production of such suitable fragments of glycoprotein Ibα, including a His$^1$-Ala$^{302}$ fragment of GPIbα expressed from mammalian cells, a tryptic fragment of GPIbα consisting of the 45 kDa residue 1–293 domain of GPIbα, glycocalicin, and glycosylated and unglycosylated peptides, derived from GPIbα, that include residue 145 thereof. Published International Application PCT/US91/0087 describes the production of a His$^1$-Ala$^{302}$ fragment (containing Thr$^{145}$) of GPIbα which mimics the proper three-dimensional conformation of that domain as expressed from full-length GPIbα in a platelet. Based on the encoding DNA thereof there may also be expressed (Example 1) a His$^1$-Ala$^{302}$ fragment encoding a Met$^{145}$ residue.

Both the Thr$^{145}$ and Met$^{145}$ forms of the His$^1$-Ala$^{302}$ fragment of GPIbα expressed as provided in Example 1 mimic the proper three-dimensional conformation of their respective domains as would be present on their respective allelic forms of GPIbα on platelets. As described in Example 2, the Met$^{145}$ alloantigenic form of GPIbα provides the antigenic epitope recognized by Sib$^a$ antibody. It is not presently known whether the epitope(s) for Sib$^a$ antibody responds to a domain of GPIbα that includes residue 145 (in methionine form and not in threonine form) or responds instead to another epitope of the molecule (a neoantigenic epitope which is only present in GPIbα when the relatively rarer Met$^{145}$ residue is present causing a conformational change in the molecule that exposes the new domain).

With respect to the production of antibodies to alloantigenic form of GPIbα (Thr/Met$^{145}$) in a patient given third-party platelets, or produced for diagnostic purposes, it is expected that such antibodies can be of both kinds, that is, dependent on epitopes distant from residue 145 but generated "conformationally" by presence of methionine, and also epitopes directly defined by and localized near the residue 145 locus. With respect to antibodies that respond to the latter kind of epitope, it is noted that peptides patterned upon the amino acid sequence of GPIbα and including residue 145 thereof, whether in glycosylated or unglycosylated form, can serve as readily synthesized antigenic material.

Production of Antibodies Against the Thr/Met$^{145}$ Alloantigenic Forms of GPIbα

Production of antibodies to the alloantigens of the invention can be accomplished following any of a number of standard procedures. Antibody appropriate for the practice of the invention may be generated by any of a number of procedures and can be polyclonal or monoclonal. For example, reference may be made to *Cellular and Molecular Immunology*, Abbas, A. K. et al. eds., Sanders Company, Philadelphia, 1991 and Eisen, H. N., General Immunology, J. P. Lippencott Company, 4th ed., Philadelphia, 1990. A preferred reference manual of techniques for producing, screening and characterizing antibodies is Harlow, E., and Lane, D., eds. *Antibodies: A Laboratory Manual*, Cold Spring Harbor Laboratory Press, Cold Spring Harbor, N.Y. (1988).

With respect to production of antibodies of the invention, one preferred approach comprises providing a clone that produces a monoclonal antibody, or providing a set of such clones which produce different monoclonal antibodies that respond to different exact epitopes dependent on Thr$^{145}$ or Met$^{145}$. Production of such antibody can be accomplished by procedures well known in the art such as that of K öhler, et al., *Eur. J. Immunol.*, 6, 292–295 (1976) wherein fusion of myeloma cells to animal lymphocytes that have been immunized with an appropriate antigen is accomplished. Suitable myeloma cell lines may be derived from BALB/c mouse MOPC 21 myelomas as described by K öhler, et al. Typically, fusion of lymphocytic cells and myeloma cells is effected by adding a suspension of lymphocytic cells to myeloma cells in the growth medium and centrifuging to form a pellet. The cells are then incubated in a growth medium containing the fusing agent. Hybridomas which synthesize and secrete antibodies are then cultured to establish continuously proliferating cell lines in tissue culture. The hybridomas are segregated into individual clones and the antibody is recovered from tissue culture thereof. A preferred reference on the production of monoclonal antibodies is *Antibodies: A Laboratory Manual*, Harlow, E and Lane, D eds., supra at pages 150–238 thereof.

A second strategy for the production of antibodies suitable in the practice of the invention comprises immunizing an animal with a peptide that includes Met$^{145}$ or Thr$^{145}$. Use of a small peptide instead of a large glycoprotein minimizes the chance that the immunized animal will make a large fraction of its antibodies to irrelevant epitopes. With respect to the production of antibody utilizing, as antigen, peptides which contain a Met or a Thr$^{145}$ residue it is preferred that such peptides be up to about 30 amino acids in length comprising fragments of GPIbα in glycosylated or nonglycosylated form. For preferred methodology, see Harlow, E., and Lane, D., supra, at pages 72–121 thereof. A polyclonal population of antibody results.

A third strategy involves generating a polyclonal response in a rabbit immunized with, for example, the residue 1-302 fragment (as Met$^{145}$) and using immune depletion of the resultant serum with the Thr$^{145}$ form of the fragment.

In addition to a complete antibody molecule there may be used in the practice of the invention any fragment thereof that contains all or a portion of the variable region thereof and therefore retains the capability of binding to all or part of a GPIbα epitope. Such suitable fragments include Fab and F(ab') fragments. With respect to the properties of the antibody or fragment thereof suitable in the practice of the invention, it is noted that an antibody, or fragment thereof having a binding affinity constant for GPIbα, or for a fragment thereof defining the epitope, of at least about 10$^5$ liters/mole is preferred.

It is noted also that techniques are available to cause the production of antibody molecules from recombinant bacterial host cells and that said antibody molecules, or fragments thereof containing the variable region thereof are also suitable in the practice of the invention.

Additional Antigens

Functionally it is noted that the invention provides a method to inhibit platelet transfusion refractoriness in a patient that comprises administering to said patient third-party platelet preparations containing GPIbα polypeptides to which the patient's immune system does not direct an antibody response. Although the invention has been described primarily in the context of a dimorphism at residue 145 of GPIbα, it is noted that additional alleles may come to be known that encode additional amino acid species at residue position 145 and that the general DNA screening procedures of the invention (see, for example, Example 2) may be used to characterize the DNA of such individuals. Similar procedures are effective at all the other amino acid sequence positions of GPIbα to identify alloantigenic loci and provide clinical procedures to compensate for amino acid polymorphisms that create such "foreign" epitopes.

Representative Diagnostic Procedures

With respect to the immunoassay procedures of the invention, it is noted that any suitable procedure which allows for the quantitative or qualitative assessment of the binding of an antibody directed to an epitope of GPIbα dependent upon the Thr/Met$^{145}$ locus thereof is effective in the practice of the invention. Such suitable procedures are outlined in Examples 3 and 4 below.

Additionally, there is hereafter described a method of double screening tissue culture supernatant from hybridoma cells to identify antibodies that are either Thr$^{145}$ or Met$^{145}$ specific. A number of different strategies can be employed, as an example—antibody capture or antigen capture (see *Antibodies: A Laboratory Manual* at page 174–195). The following describes antibody capture.

Since the antigens (recombinant pMW2/Thr$^{145}$ and pMW2/Met$^{145}$) are available in large amounts, an antibody capture is a convenient way to screen for the required hybridoma cell line. Both antigens are spotted onto nitrocellulose (NC or dot-blot) or applied onto a polyvinylchloride multiwell plate. The NC or plate is blocked with a protein solution of at least 1 µg/ml. Approximately 1 µl of hybridoma tissue culture supernatant is added to each square (NC) or 200 µl is added to the well of each plate. After an incubation for 1 hour, the NC or wells are washed 3 times with the same blocking solution. Bound antibody is detected by a second incubation with an $^{125}$I-labeled rabbit anti-mouse immunoglobulin (using approximately 50,000 cpm per NC spot or well). The wells are then washed 3 times in the same blocking solution and exposed to autoradiography (NC) or to gamma ray counting in a gamma spectrometer. This procedure will allow an identification of clones that are secreting antibodies specific for either the Thr$^{145}$ or Met$^{145}$ form of GPIbα.

Storage and Manipulation of Blood Products Containing Platelets

The procedures described above are effective for the purpose of providing antibody useful for determining whether or not a patient has been previously exposed to a third-party blood product containing platelets, the GPIbα thereof being of different alloantigenic form with respect to the Thr/Met$^{145}$ locus thereof than that of the patient.

Effective means are therefore disclosed whereby facilities that provide health care and/or store blood products containing platelets can minimize adverse immune reactions thereto in patients and maximize the effectiveness of platelet-containing transfused products. Such procedures include utilizing the diagnostic reagents provided by the invention to type donors and recipients, and to segregate supplies of platelets based on identification of the amino acid residue at position 145 of the GPIBα thereof.

Consistent with the practice of the invention, a blood bank or medical care facility should segregate blood products containing platelets into different stocks, one stock containing only platelets with GPIbα having the Thr$^{145}$ form thereof, a second stock containing platelets having only the Met$^{145}$ form thereof, and (optionally) a third stock may be prepared containing both the methionine and threonine 145 forms of GPIbα polypeptides and being suitable for administration to heterozygous individuals.

Therapeutic use of platelet stock so segregated comprises a preferred method of inhibiting hemorrhage in a patient in that the above blood products will remain effective in the patient for longer periods than products as presently administered, surviving, for example, for a longer time without being removed from circulation by the kidneys or becoming, as a result of immunological reactions, otherwise inoperable in a patient.

The distribution of the alleles encoding Thr$^{145}$ and Met$^{145}$ in the human population underscores the importance of the invention. Administration of third-party blood products containing platelets from an individual who expresses both alleles of the GPIbα-encoding gene makes likely adverse immunological reaction in a substantial portion of the human population. Similarly, individuals who are homozygous for Met$^{145}$ are at great risk for adverse clinical effects when receiving platelets from the general population.

EXAMPLES

The following examples are illustrative of the practice of the invention.

Example 1

Preparation of GPIbα polypeptide and/or fragments thereof suitable as alloantigen for the production of allotypic antibody There is hereafter described production of alloantigenic forms of GPIbα, and fragments thereof, from which may be produced allotypic antibody suitable for diagnostic purposes and having as epitope thereof either the Thr$^{145}$ or Met$^{145}$ form of GPIbα.

(A) His$^1$-Ala$^{302}$ recombinant GPIbα fragment

The construction, characterization and utilization of the expression plasmid pMW2/Thr$^{145}$ that directs secretion from mammalian cells, for example, CHO-K1 cells, of the His$^1$-Ala$^{302}$ fragment of GPIbα has been described. Murata, M. et al., *J. Biol. Chem.*, 266, 15474–15480 (1991). Further detail of the characterization of pMW2/Thr$^{145}$, the resultant polypeptide, and methods for the expression thereof, are provided in published International Application PCT/US91/0087, filed Jan. 4, 1991, including Examples 9 to 14 therein. The above publications demonstrate that this GPIbα fragment has a tertiary conformation indicative of proper folding absent expression therewith of the C-terminal half of the 610 residue full length GPIbα polypeptide. As described in the '0087 International Application, it is expected that recombinant host cell lines exist also that allow for effective expression of the full length His$^1$-Leu$^{610}$ polypeptide, and the proper folding and glycosylation thereof.

The site directed mutagenesis strategy of Murata, M. et al. (following Kunkel, T. A., *Methods. Enzymol.*, 154, 367–383 (1987)) was used to prepare the Met$^{145}$-encoding form of pMW2, wherein a Met$^{145}$ codon is substituted for a Thr$^{145}$ codon. pMW2/Thr$^{145}$ and pMW2/Met$^{145}$ can then be transfected into CHO-K1 cells using a calcium phosphate-mediated transfection procedure. Following the procedure of Murata, M. et al., stable cell lines resistant to Geneticin® antibiotic were then screened for the production of GPIbα antigen using two murine monoclonal antibodies, LJ-Ibα1 and LJ-P3 that recognize epitopes within the 45 kDa amino terminal tryptic fragment (residues 1–293) of GPIbα. See Handa, M. et al., *J. Biol. Chem.*, 1261, 12579–12585 (1986), Vicente, V. et al., *J. Biol. Chem.*, 265, 274–280 (1990).

Elements necessary for the preparation of the suitable antigenic polypeptides of the invention are: (A) DNA sequences which encode the residue His$^1$-Leu$^{610}$, His$^1$-Ala$^{302}$, or similar domains of the GPIbα polypeptide that contain the epitope(s) that reflect the Thr/Met$^{145}$ dimorphism; (B) an expression plasmid or viral expression vector capable of directing in a eucaryotic cell the expression therein of the aforementioned domains; and (C) a eucaryotic host cell in which said expression may be effected.

The GPIbα polypeptides so expressed are expected not to be secreted from host cells because of the lack of attachment to the nascent GPIbα polypeptide of a signal peptide. Purification of proteins expressed therein and the extraction of pharmacologically useful quantities thereof are expected to be more difficult than if the polypeptide could be caused to be secreted into the culture medium of the host cells.

Accordingly, in the preferred practice of the invention there is provided a GPIbα encoding DNA sequence for insertion into a suitable host cell in which there is inserted upstream from the residue 1–610 or 1–302 encoding sequence thereof a DNA sequence encoding the GPIbα signal peptide. Signal peptides corresponding to other protein species may prove equally effective to cause the secretion of GPIbα. von Heijne, G., *J. Mol. Biol.*, 184, 99–105 (1985). When attached to the amino terminal end of the residue 1–610 or 1–302 GPIb(α) polypeptide, the signal peptide causes the polypeptide to be recognized by cellular structures as a polypeptide of the kind to be processed for ultimate secretion from the cell, with concomitant cleavage of the signal polypeptide from the mature GPIbα polypeptide.

A wide variety of expression plasmids or viral expression vectors are suitable for the expression of the GPIbα polypeptides or the amino terminal regions thereof. One factor of importance in the selection of an expression system is the provision of a high efficiency transcription promoter directly adjacent to the cloned GPIbα insert. Another factor of importance in the selection of an expression plasmid or viral expression vector is the provision of an antibiotic resistance gene marker therein so that continuous selection for stable transformant eucaryotic host cells can be applied.

Examples of plasmids suitable in the practice of the invention include pCDM8, pCDM8$^{neo}$, pcDNA1, pcDNA1$^{neo}$, pMAM$^{neo}$ and Rc/CMV. Plasmids whose use in the practice of the invention is preferred include pCDM8$^{neo}$, pcDNA1$^{neo}$, pMAM$^{neo}$ and Rc/CMV. A DNA sequence encoding the GPIbα polypeptide, or a fragment thereof, may also be inserted into a plasmid or vector suitable for causing expression of the polypeptide in a bacterial system.

There can be used various viral expression vector systems in the practice of the invention, including for example, those based upon retroviruses and those based upon baculovirus *Autographa californica* nuclear polyhidrosis virus.

Representative host cells comprising permanent cell lines suitable for the practice of the invention include CHO-K1 Chinese hamster ovary cells, ATCC-CCL-61; COS-1 cells, SV-40 transformed African Green monkey kidney, ATCC-CRL 1650; ATT 20 murine pituitary cells; RIN-5F rat pancreatic β cells; cultured insect cells, *Spodoptera frugiperda*; or yeast (Sarcomyces).

(B) Preparation of additional GPIbα fragments suitable as alloantigens

Production of the 45 kDa fragment (residues 1 to 293) of GPIbα from blood has been described previously, Vicente, V. et al., *J. Biol. Chem.*, 265(1), 274–280 (1990). Preparation of glycocalicin has been described by Handa, M. et al, *J. Biol Chem.*, 261 12579–12585 (1986). The Thr$^{145}$ form of the 45 kDa fragment or of glycocalicin may be derived from individuals homozygous for GPIbα containing Thr$^{145}$ (corresponding to the first discovered allele, Lopez, J. A. et al. *Proc. Natl. Acad. Sci. USA*, 84, 5615–5617 (1987)). Met$^{145}$ forms of the above fragments may be prepared from GPIbα of individuals homozygous for the Met$^{145}$ form. Polypeptides of heterozygous individuals may be separated using, for example, immunoaffinity chromatography sensitive to the relevant difference in epitope or conformation.

Synthetic peptides containing up to about 30 amino acids, and comprising fragments of glycoprotein Ibα (containing a residue position equivalent to either Met$^{145}$ or Thr$^{145}$) can be prepared, for example, by following the method of Houghten, R. A., *Proc. Natl. Acad. Sci. USA*, 82, 5131–5135 (1985) with further purification as described in Vicente, V. et al., *J. Biol. Chem.*, 265(1), 274–280 (1990). Glycosylation may be added to such synthetic peptides by coupling at appropriate sites to mimic natural glycosylation. Alternately, sufficient quantities of peptide to serve as antigen may be derived from other fragments of GPIbα of blood products, produced therefrom, for example, by multiple proteolytic cleavages and subsequent purification, for example, by high pressure liquid chromatography.

Example 2

Determination of the identity of amino acid(s), Thr/Met, at position 145 of GPIbα polypeptide of a patient or donor using DNA restriction analysis Genomic DNA was isolated, after informed consent, from the peripheral blood lymphocytes of healthy blood donors recruited at the General Clinic Research Center facility of the Scripps Clinic, La Jolla, Calif., following procedures well known in the art. See Blin, N. et al., *Nucleic Acid Res.*, 3, 2303 (1976). The lack of introns within the coding sequence for GPIbα was exploited to permit amplification of genomic DNA fragments of the GPIbα gene to determine the allelic character of the residue 145 locus and to identify the genetic basis of the Sib$^a$ antigen. Two oligonucleotide primers, Ibα-3 (5'-GGACG----------CGGC-3') corresponding to GPIbα residues 106–112, and representing nucleotides 898–918 according to the system of Wenger, R. H. et al. and also Ibα-4 (5'-GCTTT----------TGAC-3') corresponding to GPIbα residues 296–302, and representing nucleotides 1470–1489 were used in a polymerase chain reaction (PCR) to generate a 591 base pair fragment that corresponds to the GPIbα-encoding sequence for polypeptide residues 106–302. The DNA fragment was amplified using a DNA thermal cycler (Perkin Elmer-Cetus, Berkeley, Calif.) in a final volume of 100 μl containing 10 mM Tris (pH 8.3), 50 mM KCl, 1.3 mM MgCl$_2$, 0.01% gelatin, 0.2 mM of each deoxynucleotide triphosphate, 0.5 μg of genomic DNA and 2.5 U Taq polymerase. The fragment was generated from a PCR comprising 30-cycles consisting of 94° C. for 30 seconds (s), 52° C. for 30 s, and 72° C. for 60 s. Cloning of amplified fragments into M13mp18 bacteriophage, and subsequent DNA sequence analysis were performed using standard techniques.

Figure 2:
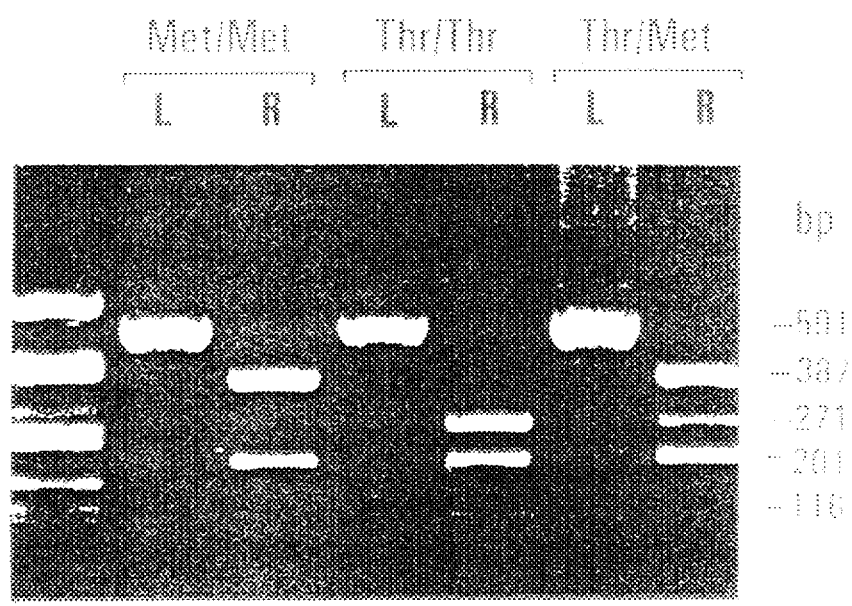

Digestion of DNA fragments derived from donors was conducted with the restriction enzyme AhaII (New England Bio-Labs, Beverly, Mass.). DNA digestion with this enzyme was allowed to proceed for 3 hours at 37° C., and the resulting products were separated and visualized in a 2% agarose gel. FIG. 1 schematically illustrates the PCR strategy used to generate a 591 base pair (bp) fragment of the GPIbα gene that codes for amino acid residues 106–302, and restriction thereof. The Thr/Met$^{145}$ amino acid dimorphism is the result of a single nucleotide transition changing the Thr codon (ACG) to a Met codon (ATG). The genotype of any individual at this locus can be determined by restriction enzyme digestion of amplified genomic DNA since the identified nucleotide transition (Thr→Met) destroys the AhaII restriction site, 5'-G(G/A)CG(T/C)C-3', (nucleotides 1016–1021, GACGCC to GATGCC) within the GPIbα-encoding DNA. Thus, the polymorphism may be analyzed by the restriction pattern of AhaII (FIG. 2).

To determine the frequency of Thr/Met$^{145}$-encoding alleles in the normal population, genomic DNA from 61 healthy blood donors was subjected to PCR analysis and digestion with AhaII. A representative agarose gel analysis (FIG. 2) shows the observed genotypes. Within the sampling of a normal population, the expected three genotypes related to codon 145 were observed. Some individuals contained two alleles coding for Met$^{145}$, some contained two alleles coding for Thr$^{145}$, and some were heterozygous containing one allele coding for Met$^{145}$ and one allele coding for Thr$^{145}$. The cumulative results revealed allele frequencies of 89% and 11% for the Thr$^{145}$ and Met$^{145}$ codons respectively. The allele frequencies within a population of restricted ethnic origin may differ from those reported herein.

PCRs were also performed on genomic DNA isolated from several healthy individuals whose platelets reacted with the anti-Sib$^a$ antibody. The amplified DNA fragments were cloned into M13mp18 for DNA sequence analysis. As compared to the published GPIbα nucleotide sequence (Lopez, J. A. et al.), the sequence analysis revealed a cytosine to thymine transition at nucleotide position 1018 in several of the cloned fragments from these individuals. The observed nucleotide transition demonstrates that the threonine$^{145}$ ACG codon, matching the reported GPIbα sequence, is substituted by a methionine$^{145}$ ATG codon in individuals showing this antibody response.

Example 3

The use of anti-Sib$^a$ antibody for the detection of Sib$^a$ antigen on platelets Serum containing the anti-Sib$^a$ antibody used in this study was obtained from the original propositus reported by Saji, H. et al., *Vox Sang*, 56, 283 (1989), and was a gift of Dr. Hiroh Saji, Kyoto Red Cross Blood Center, Kyoto, Japan. Platelet reactivity with the anti-Sib$^a$ antibody was evaluated using a modified antigen capture ELISA procedure. Ichida, F. et al., *Blood*, 78, 1722 (1991).

To perform the assays, one hundred microliters of washed platelets (1×10$^8$/ml) to be tested were mixed with 5–20 μl of the anti-Sib$^a$ serum for 1 hour at 22°–25° C., and the platelets were lysed with "PBS", phosphate buffered saline consisting of 10 mM, Na$_2$HPO$_4$, 0.14M NaCl, and containing also 10 mM EDTA and 1% Triton X-100. The lysate was centrifuged (11,750 g) to remove the insoluble debris and the supernatant was incubated (60 min) in a microtiter plate coated with the anti-GPIb-IX monoclonal antibody SZ1. The SZ1 antibody (purchased from Immunotech, Marseille, France) is directed against an epitope in the human GPIb-IX complex and was coated previously into the microtiter plate wells by an overnight incubation (3 μg/ml) at 4° C., followed by washing with PBS containing also 0.05% Tween 20. The amount of anti-Sib$^a$-antibody/Sib$^a$-antigen immune complex bound to SZ1 was determined using a biotinylated goat anti-human IgG (Tago, Burlingame, Calif.) and subsequent incubation with alkaline phosphatasestreptavidin (Zymed, San Francisco, Calif.). Color development was monitored after the addition of substrate by determining the OD$_{405}$ in a microplate reader (Bio-Rad, Richmond, Calif.). Results were expressed as an OD ratio defined as (sample OD-mean OD of negative controls)/mean OD of negative controls according to the procedure of Ichida, F. et al.

Since the Sib$^a$ antigen has been determined (see Example 2 above) to represent the GPIbα polypeptide including Met$^{145}$ at the Thr/Met$^{145}$ locus thereof, other antibodies besides Sib$^a$ that are directed to an epitope of GPIbα dependent on the presence of a Met$^{145}$ or Thr$^{145}$ residue in said polypeptide may be used similarly in the assay. Such antibodies may be a monoclonal antibody or a a polyclonal population such as from human serum.

Example 4

Immunoreactivity of the anti-Sib$^a$ antibody with recombinant GPIbα fragments

Culture medium from CHO-K1 cells transfected with either pMW2/Thr$^{145}$ or pMW2/Met$^{145}$ plasmid was assayed for the content of GPIbα antigen by a dot blot technique using a commercial apparatus (Pierce Chemical Co.). The methodology involved (Murata, M. et al., *J. Biol. Chem.*, 266, 15474 (1991)) is based on binding defined quantities of the test sample containing the antigen to circular discs of nitrocellulose membrane.

First, the total amount of GPIbα antigen was measured by determining its reactivity with a specific rabbit antiserum obtained by immunization with a synthetic peptide corresponding to GPIbα residues Gly$^{271}$-Glu$^{285}$ (Vicente, V. et al., 1990). Use of this epitope allows quantization of antigen without reference to binding affinity at, or because of, Thr$^{145}$ or Met$^{145}$. The antigen-coated membrane was incubated for 2 hours at 22°–25° C. with the anti-GPIbα$^{271-285}$ serum diluted 1:200 in Blotto (a solution composed of 50 mg/ml fat-free milk, 0.25 mM phenylmethylsulfonyl fluoride, 0.15M NaCl, in PBS). At the end of the incubation, the membrane was washed 3 times in Blotto, incubated for 1 hour with $^{125}$I-labelled goat anti-rabbit IgG, and washed again 3 times in Blotto. Discs of the nitrocellulose membrane corresponding to the position of each application well were cut out and the amount of bound radioactivity was determined with a γ-scintillation spectrometer. The amount of radioactivity bound to each application well was proportional to the amount of GPIbα antigen bound to the nitrocellulose membrane. Based on the results of this assay, culture media from CHO-K1 cells in which were present residue 1 to 302 fragments of GPIbα (as Thr or Met$^{145}$ forms) were diluted (normalized) to obtain identical amounts of GPIbα antigen.

After normalization of recombinant antigen levels, culture media were tested for their reactivity with the anti-Sib$^a$ antibody (see Example 3) using the same dot blot technique. Culture media were vacuum-drawn through a nitrocellulose membrane, blocked with Blotto for 2 hours at 22°–25° C. and then incubated for 2 hours with serum containing the anti-Sib$^a$ antibody or normal serum (1:20 dilutions). After 3 cycles of washing in Tris-buffered saline (10 mM Tris, pH 7.5, 140 mM NaCl) containing also 5% fat-free milk, the membrane was transferred into a solution of horseradish peroxidase-conjugated goat anti-human IgG (1:500. Zymed, San Francisco, Calif.) for 2 hours. The membrane was finally washed 3 times with Tris-buffered saline and incubated in a solution containing O-phenylendiamine (Zymed) and hydrogen peroxide to develop color, following manufacturer's instructions.

Since the Sib$^a$ antigen has been determined (see Example 2 above) to represent the GPIbα polypeptide including Met$^{145}$ at the Thr/Met$^{145}$ locus thereof, other antibodies besides Sib$^a$ that are directed to an epitope of GPIbα dependent on the presence of a Met$^{145}$ or Thr$^{145}$ residue in said polypeptide may be used similarly in the assay. Such antibodies may be a monoclonal antibody or a polyclonal population, such as from human serum. The antigenic properties of other fragments of GPIbα, expressing epitope dependent on the Thr/Met$^{145}$ locus, can be similarly assayed as long as they adhere to the nitrocellulose and be recognized thereon by antibody.

Example 5
Construction of Expression Vectors

A recombinant expression plasmid, pMW2, was constructed to contain a partial GP Ibα sequence (His$^1$-Ala$^{302}$) essentially corresponding to the extracytoplasmic 45 kDa domain of the molecule (His$^1$-Arg$^{293}$; Titani et al., 1987). To construct pMW2, a DNA fragment corresponding to nucleotides 503–1490 of the GP Ibα gene (Wenger et al., 1988) was synthesized in a polymerase chain reaction that added BamHI restriction sites on the ends of the amplified fragment. The synthetic BamHI fragment was cloned into M13 mp19 and sequence analysis verified a coding sequence identical to the corresponding region of the GP Ibα cDNA (Lopez et al., 1987). The GP Ibα insert of the M13 construct was recloned as an EcoRI-XbaI fragment into the bacterial plasmid pBS/KS- (Stratagene). This strategy was possible as a result of the initial cloning into M13 mp19 and the acquisition of EcoRI and XbaI restriction sites from the M13 polylinker sequence. The GP Ibα insert of the pBS/KS- construct was finally cloned into the plasmid pCDM8$^{neo}$, and the resultant recombinant molecule was designated pMW2. Cloning of the GP Ibα fragment from the pBS/KS- construct into pCDM8$^{neo}$ utilized two unique restriction sites acquired from the pBS/KS-polylinker sequence: an XhoI site located 5' to the GP Ibα initiating methionine codon and a NotI site located 3' to the codon for mature GP Ibα residue 302. pCDM8$^{neo}$ contains a neomycin resistance gene within the eukaryotic expression plasmid pCDM8 (Seed 1987). The expression construct, pMW2, contains coding sequence that predictably synthesizes a primary translation product containing the GP Ibα signal peptide, the sequence of the mature protein between residues 1 and 302, and an additional 7-residue COOH-terminal sequence, unrelated to GP Ibα and preceding the first in-frame termination codon, TAG.

Cell Culture and Transfection

Chinese hamster ovary cells (CHO-K1) were cultered in Dulbecco's modified Eagle medium supplemented with 0.5 mM nonessential amino acids (Whittaker), 2.5 mM L-glutamine, and 10% heat-inactivated fetal calf serum (GIBCO). Cells from confluent cultures were harvested with 0.25% trypsin, 0.2% EDTA, grown for 1 day in 60-mm dishes (1.2×10$^5$ cells/dish seeding density) and transfected with 10 μg of the appropriate plasmid DNA using the calcium phosphate-mediated transfection procedure (Chen and Okayama, 1987). At 48 h of post-transfection, cells were harvested with trypsin-EDTA and 1.2×10$^4$ cells were plated on a 60-mm dish. Cells were cultured for 14 days in medium containing 10% fetal calf serum, L-glutamine, nonessential amino acids, and 800 μg/ml of Geneticin (Sigma). Independent clones were picked using cloning rings and grown in 12-well plates in medium containing Geneticin for 7 days. Two different anti-GPIbα antibodies were used in dot-blot analysis for the identification of clones expressing recombinant protein: LJ-P3, that detects a native conformation-dependent epitope in the amino-terminal 45 kDa tryptic fragment of the protein (Handa et al., 1986), and LJ-Ibα1, which reacts with an epitope located between residues 1–237 and is not dependent on the native conformation of the protein. In fact, the antibody reacts more strongly with SDS-denatured and reduced GP Ibα than native GP Ibα (Vicente et al., 1988).

Deposit of Strains Useful in Practicing the Invention

A deposit of biologically pure culture of the following strain was made under the Budapest Treaty with the American Type Culture Collection, 12301 Parklawn Drive, Rockville, Md., the accession number indicated was assigned after successful viability testing, and the requisite fees were paid.

Access to said culture will be available during pendency of the patent application to one determined by the Commissioner of the United States Patent and Trademark Office to be entitled thereto under 37 C.F.R. §1.14 and 35 U.S.C. §122, or if and when such access is required by the Budapest Treaty. All restriction on availability of said culture to the public will be irrevocably removed upon the granting of a patent based upon the application and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture(s) of the same taxonomic description.

| Strain/Plasmid | ATCC No. | Deposit Date |
|---|---|---|
| E. coli XS127 pMW2 (Met$^{145}$)(TSRI 278.0) | ATCC 68886 | 1/2/92 |

We claim:

1. A method of immunoassay utilizing a monoclonal antibody, or an antigen binding fragment thereof, wherein said monoclonal antibody or antigen binding fragment binds to a glycoprotein Ibα polypeptide having a Met[145] residue, and wherein said monoclonal antibody or antigen binding fragment does not bind to a glycoprotein Ibα polypeptide having a $Thr^{145}$ residue, said method comprising contacting said monoclonal antibody with glycoprotein Ibα polypeptide or a fragment thereof containing a $Met^{145}$ or $Thr^{145}$ residue and detecting whether there is present a complex of said monoclonal antibody or antigen binding fragment thereof and said $Met^{145}$ form of said glycoprotein or said fragment thereof.

2. A method according to claim 1 wherein said monoclonal antibody has a binding affinity constant for said glycoprotein Ibα, or fragment thereof, of at least about $10^5$ liter/mole.

3. A method of detecting an antibody to a glycoprotein Ibα polypeptide having a $Met^{145}$ residue, wherein said antibody binds to a glycoprotein Ibα polypeptide having a $Met^{145}$ residue, and wherein said antibody does not bind to a glycoprotein Ibα polypeptide having a $Thr^{145}$ residue, said method comprising contacting a sample of blood, or a composition derived therefrom, with a recombinantly prepared alloantigenic $Thr^{145}$ or $Met^{145}$ form of glycoprotein Ibα, or a recombinantly prepared fragment thereof, wherein said fragment contains the $Thr^{145}/Met^{145}$ residue and detecting whether there is present a complex of said antibody and said Met$^{145}$ form of said glycoprotein or said fragment thereof.

4. A method according to claim 3 wherein the recombinantly prepared alloantigenic Thr$^{145}$ or a recombinantly prepared Met$^{145}$ form of glycoprotein Ibα, or fragment thereof containing the Thr$^{145}$/Met$^{145}$ locus, used to determine the presence of anti-glycoprotein Ibα antibody in the blood of a patient or donor is selected from the group consisting of (A) the Thr$^{145}$ or Met$^{145}$ form of glycoprotein Ibα;

(B) the Thr$^{145}$ or Met$^{145}$ form of a fragment of glycoprotein Ibα comprising residues 1 to 300 thereof;

(C) the Thr$^{145}$ or Met$^{145}$ form of glycocalicin; and (D) the Thr$^{145}$ or Met$^{145}$ form of a peptide containing up to 30 amino acids, said peptide consisting of a fragment of glycoprotein Ibα polypeptide in glycosylated or non-glycosylated form and containing residue 145 of glycoprotein Ibα.

* * * * *